(12) United States Patent
Filer

(10) Patent No.: US 7,820,851 B2
(45) Date of Patent: Oct. 26, 2010

(54) ISOTOPICALLY LABELED POLYFLUORINATED COMPOUND USEFUL AS AN IMAGING TRACER

(75) Inventor: Crist N. Filer, Somerville, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 11/859,937

(22) Filed: Sep. 24, 2007

(65) Prior Publication Data

US 2008/0089847 A1 Apr. 17, 2008

Related U.S. Application Data

(60) Provisional application No. 60/827,283, filed on Sep. 28, 2006.

(51) Int. Cl.
*C07C 69/63* (2006.01)
*C07C 53/21* (2006.01)
*C07C 19/08* (2006.01)

(52) U.S. Cl. .......................... 560/227; 562/605; 570/134
(58) Field of Classification Search ........................ None
See application file for complete search history.

(56) References Cited

U.S. PATENT DOCUMENTS 5,312,935 A * 5/1994 Mayer et al. ................. 554/182
5,466,877 A * 11/1995 Moore ......................... 562/852

OTHER PUBLICATIONS

Mathis et al., International Journal of Chemical Kinetics (1982), 14(5), 565-83.*
Knickelbein et al., Journal of Physical Chemistry (1984), 88(10), 2017-24.*

* cited by examiner

*Primary Examiner*—Karl J Puttlitz
(74) *Attorney, Agent, or Firm*—Gifford, Krass, Sprinkle, Anderson & Citkowski, P.C.

(57) ABSTRACT

A polyfluorinated compound is provided inclusive of at least one $^{18}$F atom having a formula:

$$CF_3(CF_2)_n R^1 \qquad (I)$$

where $R^1$ is —C(O)OR$^2$, —C(O)N(R$^3$)$_2$, C—N(R$^3$)$_2$, —C(NR$^3$)R$^2$, C-QR$^3$, -QR$^3$, —N$^+$(R$^3$)$_3$, X, C$_1$-C$_{30}$ alkyl, C$_1$-C$_{30}$ haloalkyl, C$_1$-C$_{30}$ alkoxyl, or C$_1$-C$_{30}$ perhaloalkyl; R$^2$ is M$^{Z+}$, H, C$_1$-C$_{12}$ alkyl, C$_1$-C$_{12}$ alkyl, C$_1$-C$_{12}$ perhalo alkyl, C$_6$-C$_{30}$ aryl, C$_6$-C$_{30}$ perhaloaryl, and a substituted form thereof where one or more protons or halogens is replaced with a plasma solubility enhancing moiety of —N$^+$(R$^3$)$_3$, —SO$_3$H, —SO$_2$N(R$^3$)$_2$, or -QR$^3$; R$^3$ is independently in each occurrence M$^{Z+}$, —SO$_3$H, —SO$_2$N(R$^3$)$_2$, or -QR$^3$; Q is O or S; M$^{Z+}$ is a cation that forms a net neutral compound with an anionic (CF$_3$(CF$_2$)$_n$C(O)O$^-$)$_Z$ and is an alkali metal cation, an alkali earth cation, a transition metal cation, ammonium, and aluminum cations; Z is an integer value of between 1 and 3 inclusive; X is a fluorine, chlorine, bromine or iodine atom; halo denotes a replacement of at least one and not all protons with X; perhalo denotes a replacement of all protons with X; and n is an integer value of between 1 and 30 inclusive.

14 Claims, No Drawings

ISOTOPICALLY LABELED POLYFLUORINATED COMPOUND USEFUL AS AN IMAGING TRACER

CROSS REFERENCE TO RELATED APPLICATIONS

This application claims priority of U.S. Provisional Patent Application Ser. No. 60/827,283 filed Sep. 28, 2006, which is incorporated herein by reference.

FIELD OF THE INVENTION

This invention relates in general to fluorochemical compositions for biological imaging, particularly labeled perfluorooctanoic acid and derivatives thereof for assessing cell or tissue distribution using imaging tools such as positron emission tomography (PET) or single-photon emission computed tomography (SPECT).

BACKGROUND OF THE INVENTION

Fluorochemicals are compounds in which some or all the carbon-hydrogen bonds are each replaced by carbon-fluorine bonds. These carbon-fluorine bonds are some of the strongest in nature and contribute to the unique stability of fluorochemicals.

Perfluorooctanoic acid (PFOA), also known as C8, is an artificial acid that has many industrial uses. PFOA and related substances are synthetic fluorochemicals useful for processing agents for manufacturing fluoropolymers and do not naturally occur in nature. Fluoropolymers with their many beneficial attributes are employed in widespread industrial settings including the textile, aerospace, electrical, and building construction industries.

PFOA designates the acid itself, and is also commonly used to refer to salts thereof such as ammonium perfluorooctanoate. One of the most common uses of PFOA is for processing polytetrafluoroethylene PTFE. PFOA is also a byproduct of the telomerization process. The telomerization process produces perfluorinated alcohol, which is commonly used in many household surface finishes and indirect contact applications in flexible food packaging. The PFOA byproduct is also in the fabrication of water- and stain-resistant clothes and other materials; aqueous film forming foam (AFFF); and in food packaging. Fluorotelomeric compounds are used in food packaging to make them resistant to grease; however, these fluorotelomeric compounds are metabolized PFOA. These compounds have been used in microwave popcorn bags, fast food and candy wrappers, and pizza box liners. In particular, microwave popcorn bags have the high fluorotelomer content, and the high cooling temperatures increase the migration of these chemicals into the popcorn oil. It is estimated that microwave popcorn accounts for more than 20% of the average PFOA levels measured in American residents. Its elimination half-life is reported as being 4 years.

Durability of PFOA prevents it from breaking down once in the environment, leading to widespread buildup and bioaccumulation in food chains. Traces of PFOA-family chemicals can now be found in the blood of nearly all Americans and in the environment worldwide and environmental regulatory agencies have become increasingly concerned about possible adverse health effects in animals and humans. Accordingly, information regarding cellular and or tissue distribution and metabolism PFOA and related substances in humans, animals, birds, fish, insects, and plants would be instrumental in evaluating concerns.

The elimination, tissue distribution, and metabolism of PFOA were previously examined in male and female rats (Vanden Heuvel J. P. et al., *J. Biochem. Toxicol.* 1991, 6(2): 83-92) wherein PFOA was labeled with carbon-14. Female rats were found to have eliminated PFOA-derived radioactivity rapidly in the urine. In the same period, male rats were observed to have eliminated only 6% of the administered carbon-14 in the urine. Analysis of PFOA-derived carbon-14 in tissues showed that the liver and plasma of male rats and the liver, plasma, and kidney of female rats were the primary tissues of distribution. Due to inherent detection limitations, this reference, however, fails to provide visualized imaging information regarding distribution and metabolism of PFOA.

U.S. Pat. No. 6,445,449 describes a method and an apparatus for determining the presence, in a sample, of compounds having carbon-halogen bonds and, in particular, carbon-fluorine bonds. The method uses pulsed laser Raman spectroscopy to detect carbon-halogen bonds, using an effect of inelastic scattering of light. The method does not identify a halocarbon compound, but instead the presence of a carbon-halogen bond is determined, using the carbon-halogen bond as a chemical tracer for the halocarbon. The method is useful for analysis of fluoroorganic compounds at ppm-ppb level for pharmaceutical, biological, medical and biomedical applications. This method, however, does not address how a compound having the carbon-halogen bond would distribute within a subject, much less the distribution information in a visualized imaging format.

Thus, there exists a need for a composition and a process for concurrently and visually accessing both the tissue distribution and cellular metabolism of PFOA and related substances in a living subject or a biological sample thereof using visualizing imaging tools such as PET or SPECT.

SUMMARY OF THE INVENTION

A polyfluorinated compound is provided inclusive of at least one $^{18}$F atom having a formula:

$$CF_3(CF_2)_nR^1 \qquad (I)$$

where $R^1$ is $-C(O)OR^2$, $-C(O)N(R^3)_2$, $C-N(R^3)_2$, $-C(NR^3)R^2$, $C-QR^3$, $-QR^3$, $-N^+(R^3)_3$, X, $C_1$-$C_{30}$ alkyl, $C_1$-$C_{30}$ haloalkyl, $C_1$-$C_{30}$ alkoxyl, or $C_1$-$C_{30}$ perhaloalkyl; $R^2$ is $M^{Z+}$, H, $C_1$-$C_{12}$ alkyl, $C_1$-$C_{12}$ alkyl, $C_1$-$C_{12}$ perhalo alkyl, $C_6$-$C_{30}$ aryl, $C_6$-$C_{30}$ perhaloaryl, and a substituted form thereof where one or more protons or halogens is replaced with a plasma solubility enhancing moiety of $-N^+(R^3)_3$, $-SO_3H$, $-SO_2N(R^3)_2$, or $-QR^3$; when $R^1$ is $-QR^3$, M is H or F; $R^3$ is independently in each occurrence $M^{Z+}$, $-SO_3H$, $-SO_2N(R^3)_2$, or $-QR^3$; Q is O or S; $M^{Z+}$ is a cation that forms a net neutral compound with an anionic $(CF_3(CF_2)_nC(O)O^-)_Z$ and is an alkali metal cation, an alkali earth cation, a transition metal cation, ammonium, and aluminum cations; Z is an integer value of between 1 and 3 inclusive; X is a fluorine, chlorine, bromine or iodine atom; halo denotes a replacement of at least one and not all protons with X; perhalo denotes a replacement of all protons with X; and n is an integer value of between 1 and 30 inclusive. The compound when mixed with a suitable carrier is particularly well suited for monitoring the distribution and metabolism of fluorinated environmental contaminants such as perfluorooctanoic acid, metabolites thereof, and related compounds that vary in carbon chain length. Upon administration to a subject and after allowing sufficient time for the compound to distribute within the subject, scanning the subject to obtain a first scan for emission from $^{18}$F radioisotope associated with the compound using a spatially resolving imaging tool, is it possible to assess the distribution and metabolism of the tracer.

DETAILED DESCRIPTION OF THE PREFERRED EMBODIMENTS

The present invention has utility as an $^{18}$F labeled tracer for visually assessing distribution and metabolism of perfluorooctanoic acid and related substances in a subject or in a biological sample derived therefrom.

As used herein, a "subject" is a mammal and includes a human and non-human subjects of non-human primates, horses, goats, cows, sheep, pigs, dogs, cats, and rodents.

As used herein, a "biological sample" is in a form of either a liquid or a solid or a combination thereof, a tissue section, a blood aliquot, a urine aliquot, a cell culture, a skin biopsy, a hair fraction, a cerebral fluid aliquot, or a saliva aliquot derived from a subject.

A tracer is provided for assessing biological distribution and metabolism of perfluorooctanoic acid (PFOA) metabolites and related substances, fluorocompounds, and environmental contaminants in a pharmaceutically acceptable carrier. The tracer contains a compound of the formula $$CF_3(CF_2)_nR^1 \quad (I)$$

where $R^1$ is —C(O)OR$^2$, —C(O)N(R$^3$)$_2$, C—N(R$^3$)$_2$, —C(NR$^3$)R$^2$, C-QR$^3$, -QR$^3$, —N$^+$(R$^3$)$_3$, X, C$_1$-C$_{30}$ alkyl, C$_1$-C$_{30}$ haloalkyl, C$_1$-C$_{30}$ alkoxyl, or C$_1$-C$_{30}$ perhaloalkyl; $R^2$ is M$^{Z+}$, H, C$_1$-C$_{12}$ alkyl, C$_1$-C$_{12}$ alkyl, C$_1$-C$_{12}$ perhalo alkyl, C$_6$-C$_{30}$ aryl, C$_6$-C$_{30}$ perhaloaryl, and a substituted form thereof where one or more protons or halogens is replaced with a plasma solubility enhancing moiety of —N$^+$(R$^3$)$_3$, —SO$_3$H, —SO$_2$N(R$^3$)$_2$, or -QR$^3$; R$^3$ is independently in each occurrence M$^{Z+}$, —SO$_3$H, —SO$_2$N(R$^3$)$_2$, or -QR$^3$; Q is O or S; when R$^1$ is -QR$^3$, M is H or F; M$^{Z+}$ is a cation that forms a net neutral compound with an anionic (CF$_3$(CF$_2$)$_n$C(O)O$^-$)$_Z$ and is an alkali metal cation, an alkali earth cation, a transition metal cation, ammonium, and aluminum cations; Z is an integer value of between 1 and 3 inclusive; X is a fluorine, chlorine, bromine or iodine atom; halo denotes a replacement of at least one and not all protons with X; perhalo denotes a replacement of all protons with X; and n is an integer value of between 1 and 30 inclusive, wherein the Formula (I) comprises at least one $^{18}$F atom.

Compounds are generally described herein using standard nomenclature. For compounds having asymmetric centers, it is understood that (unless otherwise specified) all of the optical isomers, enantiomers, racemates and stereoisomers, as well as all pharmaceutically acceptable salts of such compounds and mixtures thereof, are encompassed. Compound descriptions are intended to encompass compounds with all possible isotopes of atoms occurring in the compounds unless otherwise noted in particular embodiments. Isotopes are those atoms having the same atomic number but different mass numbers. By way of general example, and without limitation, isotopes of hydrogen include tritium and deuterium and isotopes of carbon include $^{11}$C, $^{13}$C and $^{14}$C. Unless otherwise specified, each variable within such a formula is defined independently of any other variable, and any variable that occurs more than one time in a formula is defined independently at each occurrence.

A "pharmaceutically acceptable salt" of an inventive compound of Formula (I) recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines of Formula (I), as well as alkali or organic salts of acidic residues such as carboxylic acids of Formula (I). Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic. Similarly, pharmaceutically acceptable cations include, but are not limited to, sodium, potassium, calcium, aluminum, lithium, and ammonium. Those of ordinary skill in the art recognize further pharmaceutically acceptable salts for the compounds provided herein, including those listed by Remington's Pharmaceutical Sciences, 17th ed., Mack Publishing Company, Easton, Pa., p. 1418 (1985). In general, a pharmaceutically acceptable acid or base salt is synthesized from a parent compound to neutralize a basic or acidic moiety therein by any conventional chemical method. Briefly, such salts are prepared by reacting the free acid or free base forms of these parent compounds with a stoichiometric excess of an appropriate base or acid, respectively. The neutralization reaction occurs in water or in an organic solvent, or in a mixture of the two; generally, the use of nonaqueous media, such as ether, ethyl acetate, ethanol, isopropanol, or acetonitrile, is preferred.

Also provided herein are proforms of an inventive compound of Formula (I). A "proform" is a compound that may not fully satisfy the structural requirements of the compounds provided herein, but is modified in vivo, following administration to a patient, to produce a compound of Formula (I). For example, a proform is an acylated derivative of a compound as provided herein. Proforms include compounds wherein hydroxy, amine or sulfhydryl groups are bonded to any group that, when administered to a subject, cleaves to form a free hydroxyl, amino or sulfhydryl group, respectively. Examples of proforms include, but are not limited to, acetate, formate, phosphate and benzoate derivatives of alcohol and amine functional groups within the inventive compounds of Formula (I) provided herein. Proforms of the compounds provided herein are prepared by modifying functional groups present in the compounds in such a way that the modifications are cleaved in vivo to yield the parent compounds.

As used herein, the term "alkyl" refers to a straight chain or branched chain saturated aliphatic hydrocarbon and optionally bearing a solubility in blood plasma enhancing moiety. Representative alkyl groups methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl.

As used herein, the term "aryl" refers to monocyclic or bicyclic aromatic rings having 6 to 30 carbon atoms each ring of which optionally bearing a solubility in blood plasma enhancing moiety. Representative aryl groups include phenyl, naphthyl, biphenyl and diphenyl.

As used herein, the term "alkoxy" refers to an alkyl group having an oxygen atom bonded to an alkyl carbon optionally bearing a solubility in blood plasma enhancing moiety. Representative alkoxy groups include methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy and 3-methylpentoxy.

As used herein, the term "halogen" refers to fluorine, chlorine, bromine and iodine.

The prefix "halo" is used to mean the replacement of at least one, but not an aliphatic protein of a moiety with a halogen.

The prefix "perhalo" is used to mean all the aliphatic protons of a moiety with a halogen.

As used herein, the term "substituent" refers to a blood plasma solubility enhancing molecular moiety that is covalently bonded to a group in replacement of an aliphatic proton.

An inventive compound of Formula (I) is optionally isotopically-labeled with an atom of the same element having an atomic mass or mass number different from the atomic mass or mass number usually found in nature. Examples of other isotopes that are optionally present in the compounds provided herein include isotopes of hydrogen, carbon, nitrogen, oxygen, phosphorus, and chlorine, such as $^2H$, $^3H$, $^{11}C$, $^{13}C$, $^{14}C$, $^{15}C$, $^{18}O$, $^{17}O$, $^{31}P$, $^{32}P$, $^{35}S$, and $^{36}Cl$. In a particular situation, substitution with heavy isotopes such as deuterium affords certain therapeutic advantages resulting from greater metabolic stability, for example increased in vivo half-life, while other isotopes such as tritium or $^{14}C$ provide an emission signal detectable by a spectrally resolving imaging tool in concert with or in a separate scan relative to $^{18}F$ spectral resolution. At least one radioactive fluorine-18 molecule is incorporated into the compound, and preferably two or more of the fluorine atoms in an inventive compound are fluorine-18.

An inventive compound of Formula (I) is optionally labeled by carrying out synthesis using precursors of at least one labeling isotope per compound of Formula (I) atom. Tritium labeled compounds may also be prepared catalytically via platinum-catalyzed exchange in tritiated acetic acid, acid-catalyzed exchange in tritiated trifluoroacetic acid, or exchange with tritium gas under heterogeneous catalysis using the compound as substrate. In addition, certain precursors are subjected to tritium-halogen exchange with tritium gas, tritium gas reduction of unsaturated bonds, or reduction using sodium borotritide, as appropriate. Preparation of radiolabeled compounds is performed by a radioisotope supplier specializing in custom synthesis of radiolabeled probe compounds.

Radiolabeling with fluorine-18 is accomplished using a variety of methods. An exemplary method for preparing $^{18}F$ labeled compounds includes direct labeling of the compound with Kryptofix® 222 also chemically known as 4,7,13,16,21,24-Hexaoxa-1,10-diazabicyclo[8,8,8]hexacosane $^{18}F$.

An effective amount is defined as the amount necessary or sufficient to render detectable the presence of PFOA and related substance in a subcellular compartment, in a cell, in a tissue, or in an organ. The effective amount varies depending on factors such as tissue or cell type, exact chemical identity of an inventive compound of Formula (I), route of administration, and the size of a sample or of a subject. Those skilled in the art empirically are able to determine the effective amount of a particular compound alone or in conjunction with another agent for the detection.

An inventive compound of Formula (I) is administered as neat compound, or as a tracer together with at least one physiologically acceptable carrier and optionally with an excipient, adjuvant, diluent, or a combination thereof. Pharmaceutical tracers are preferably formulated for oral delivery to a human or other subject.

Pharmaceutical carriers are of sufficiently high purity and sufficiently low toxicity to render them suitable for administration to the animal being treated. The carrier is either inert or possesses pharmaceutical benefits. The amount of carrier employed in conjunction with the compound is sufficient to provide a practical quantity of material for administration per unit dose of the compound. Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil and corn oil; polyols such as propylene glycol, glycerine, sorbitol, mannitol and polyethylene glycol; alginic acid; phosphate buffer solutions; emulsifiers, such as the Tweens; wetting agents, such as sodium lauryl sulfate; coloring agents; flavoring agents; tableting agents; stabilizers; antioxidants; preservatives; pyrogen-free water; isotonic saline; and phosphate buffer solutions.

An effective amount of one or more of the inventive compounds provided herein is mixed with a suitable pharmaceutical carrier, excipients, adjuvant or vehicle. In instances in which the compounds exhibit insufficient solubility, methods for solubilizing compounds may be used. Such methods are known to those of skill in this art and include, but are not limited to, using co-solvents such as dimethylsulfoxide (DMSO), using surfactants such as Tween, or dissolution in aqueous sodium bicarbonate.

Derivatives of the compounds, such as salts of the compounds or prodrugs of the compounds are also used in formulating effective pharmaceutical compositions. Upon mixing or addition of the compound(s), the resulting mixture is a solution, suspension, emulsion or the like. The form of the resulting mixture depends upon a number of factors, including the intended mode of administration and the solubility of the compound in the chosen carrier or vehicle. An inventive composition containing a compound of Formula (I) is administered orally, topically, parenterally, by inhalation or spray, sublingually, transdermally, via buccal administration, rectally, as an ophthalmic solution, or by other means, in dosage unit formulations.

Dosage formulations suitable for oral use include, for example, tablets, troches, lozenges, aqueous or oily suspensions, dispersible powders or granules, emulsions, hard or soft capsules, or syrups or elixirs. Compositions intended for oral use are prepared according to any method known to the art for the manufacture of pharmaceutical compositions. Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations optionally contain a demulcent.

In one particular embodiment of the present invention, an inventive compound of Formula (I) is incorporated into oral liquid preparations such as, for example, aqueous or oily suspensions, solutions, emulsions, syrups or elixirs. Moreover, formulations are optionally presented as a dry product for constitution with water or other suitable vehicle before use. Such liquid preparations contain conventional additives, such as suspending agents (e.g., sorbitol syrup, methyl cellulose, glucose/sugar, syrup, gelatin, hydroxyethyl cellulose, carboxymethyl cellulose, aluminum stearate gel and hydrogenated edible fats), emulsifying agents (e.g., lecithin, sorbitan monsoleate or acacia), non-aqueous vehicles, which can include edible oils (e.g., almond oil, fractionated coconut oil, silyl esters, propylene glycol and ethyl alcohol) and preservatives (e.g., methyl or propyl p-hydroxybenzoate and sorbic acid).

For a suspension, typical suspending agents include methylcellulose, sodium carboxymethyl cellulose, hydroxylpropylmethylcellulose, Avicel® RC-591, polyvinylpyrrolidone, gum tragacanth, gum acacia and sodium alginate; typical wetting agents include lecithin and polysorbate 80, polyoxyethylene stearate, heptadecaethyleneoxycetanol, polyoxyethylene sorbitol substitute, polyethylene sorbitan substitute; and typical preservatives include methyl paraben and sodium benzoate, ethyl or n-propyl p-hydroxybenzoate.

Oily suspensions are formulated by suspending the active ingredients in a vegetable oil, for example peanut oil, olive oil, sesame oil or coconut oil, or in a mineral oil such as liquid paraffin. The oily suspensions optionally contain a thickening agent, for example beeswax, hard paraffin or cetyl alcohol. Sweetening agents, such as those set forth above, and flavoring agents may be added to provide palatable oral preparations. These compositions are preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

In another particular embodiment, an inventive compound of the present invention is formulated into tablets typically containing conventional pharmaceutically compatible adjuvants as inert diluents, such as calcium carbonate, sodium carbonate, mannitol, lactose and cellulose; binders such as starch, gelatin and sucrose; disintegrants such as alginic acid and croscarmellose; lubricants such as magnesium stearate, stearic acid and talc. Glidants such as silicon dioxide can be used to improve flow characteristics of the powder mixture. Coloring agents, such as FDC dyes, are optionally added for appearance. Sweeteners and flavoring agents, such as aspartame, saccharin, menthol peppermint and fruit flavors, are useful adjuvants for chewable tablets.

Capsules (including time release and sustained release formulations) typically include one or more solid diluents disclosed above. The selection of carrier components often depends on secondary considerations like taste, cost and shelf stability. Such compositions are optionally coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac. Formulations for oral use are optionally presented as hard gelatin capsules wherein an inventive compound of Formula (I) is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

In yet another particular embodiment of the present invention, an inventive composition containing a compound of Formula (I) is in the form of a sterile injectable aqueous or oleaginous suspension. Such a suspension is formulated according to the known art using dispersing or wetting agents and suspending agents as described above. The sterile injectable preparation are either sterile injectable solution or suspension in a non-toxic parentally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium. For this purpose any bland fixed oil is employed including synthetic mono- or diglycerides. In addition, fatty acids such as oleic acid are useful in the preparation of injectables.

The composition containing a compound of Formula (I) is optionally injectable parenterally in a sterile medium. Parenteral administration includes subcutaneous injections, intravenous, intramuscular, intrathecal injection or infusion techniques. The inventive composition, depending on the vehicle and concentration used, is either suspended or dissolved in the vehicle. Adjuvants such as local anesthetics, preservatives and buffering agents are also dissolved in the vehicle. In many compositions for parenteral administration, the carrier comprises at least about 90% by weight of the total composition. Preferred carriers for parenteral administration include propylene glycol, ethyl oleate, pyrrolidone, ethanol and sesame oil.

For in vitro studies, an inventive composition is administered to a biological sample and the composition is allowed to react with the sample for a period of time. The length of the period depends on the type of the sample in study and the particular detectable moieties used to label the composition.

The amount of radiation emission needed for detection is readily determined by one of skill in the art. Factors relevant in determining the amount of Rads needed includes, sample mass, whether the inventive compound is mono or poly-labeled with $^{18}$F, clearance time, and whether the sample is in vivo or in vitro.

Within in vitro methods for determining the presence or absence of PFOA and derivatives thereof in a sample, a sample is incubated with a compound as provided herein under conditions that permit tissue incorporation and or cellular internalization of the compound. The amount of compound internalized in the sample is then detected. For example, a compound is labeled using any of a variety of well-known techniques (e.g., radiolabeled with a radionuclide such as fluorine-18, as described herein), and incubated with the sample (which may be, for example, a preparation of cultured cells, a tissue preparation or a fraction thereof). A suitable incubation time is generally determined by assaying the level of internalization that occurs over a period of time. Following incubation, uninternalized compound is removed, and bound compound detected using any method for the label employed (e.g., autoradiography or scintillation counting for radiolabeled compounds; spectroscopic methods may be used to detect luminescent groups and fluorescent groups). As a control, a matched sample is simultaneously contacted with radiolabeled compound and a greater amount of unlabeled compound. Unbound labeled and unlabeled compound is then removed in the same fashion, and bound label is detected. A greater amount of detectable label in the test sample than in the control indicates the greater internalization of PFOA and derivatives thereof in the sample.

Within separate aspects, the present invention provides a variety of in vitro uses for the compounds provided herein. For example, such compounds are used as probes for the detection and localization of PFOA, metabolites; analogs such as perfluoromonoic acid, perfluorodecanoic acid, and analog metabolites, in samples such as tissue sections, or as radiotracers for positron emission tomography (PET) imaging or for single photon emission computerized tomography (SPECT). Such assays are used to characterize PFOA and derivative thereof in living subjects.

When positron emission tomography (PET) is employed as an imaging tool, an inventive composition is optionally labeled with a second isotope of short half life such as carbon- 11 (~20 min), nitrogen-13 (~10 min), or oxygen-15 (~2 min), or delivered in concert with a compound that varies from that of Formula (I) in lacking $^{18}$F and including another positron or photon emitting isotope.

An inventive compound of the present invention, labeled with fluorine-18 described as above, is administered to a subject and detected using PET scanning. The fluorine-18 labeled ($^{18}$F-labeled) compound is an analog tracer for PFOA ingested or inhaled by the subject. A typical dose of $^{18}$F-labeled compound used in an oncological scan is 200-400 MBq for an adult human. After a period of time typically within the range of 20 minutes to 3 hours, the $^{18}$F-labeled compound stops traveling and is instead trapped in a particular cell type. This results in intense radiolabeling of tissues or cells thereof with high uptake of the $^{18}$F-labeled compound. The subject is then analyzed for PET scanning for both the localization of the radiolabeled compound and the quantification of the accumulation of the compound. The results derived from the PET scanning provide firsthand information of how an environmental contaminant fluorocompound distributes and metabolizes in the subject. As a result, when coupled with PET, $^{18}$F-labeled compound of Formula (I) is useful for diagnosing, staging, and monitoring PFOA accumulation and metabolism in vivo.

Images obtained from PET or SPECT are displayed with a variety of software packages such as the Living Image software from Xenogen. Optionally successive scans in PET, SPECT, or alternating tomography instruments such as PET then SPECT provide temporal distribution and clearance data. Multiple scans are readily overlapped to provide additional insights. Images from microPET and microCAT are viewed using ASIPro (Siemens Preclinical Solutions, Knoxville, Tenn.), Amide (Loening A. M., Gambhir S. S.; AMIDE: A free software tool for multimodality medical image analysis. *Mol. Imaging* 2:131-137; 2003), or JANUS.

Example Preparation of [18F] Perfluorooctanoic Acid

Perfluorooctanoic Acid (2 mg) in 1 mL of DMSO was added to dried K[$^{18}$F]F

Kryptofix 2.2.2 complex (10 mg) and heated at 100° C. for 15 minutes. After the labelling, 10 mL of water was added to the cooled reaction vessel and the crude reaction mixture was eluted through a C-18 Sep Pak to retain the crude [$^{18}$F] product. The C-18 Sep Pak was eluted with another 10 mL of water followed by separate elution with 1 mL of ethanol. The ethanol fraction was injected onto a semi-preparative reverse phase HPLC column eluted with the solvent system 0.1% aqueous trifluoroacetic acid:acetonitrile (60:40) and pure [$^{18}$F] perfluorooctanoic acid was obtained through fluorine exchange between the native compound and K[$^{18}$F]F with stoichiometry therebetween controlling the average number of $^{18}$F per labeled compound molecule. The $^{18}$F product was injected onto to a reverse phase analytical HPLC column eluted with the same solvent system and co-injected with authentic unlabelled Perfluorooctanoic acid to confirm identity. A labeled product is obtained under microwave irradiation with accelerated reaction times thereby providing a higher active dosimetry during a scan.

REFERENCES

Flaherty J. M. et al. Quantitative determination of perfluorooctanoic acid in serum and plasma by liquid chromatography tandem mass spectrometry; *J. Chrom. B.* 819, 329-338 (2005).
Hansen, K. J., Johnson, H. O., Eldridge, J. S., Butenhoff, J. L., and Dick, L. A. (2002). Quantitative Characterization of Trace Levels of PFOS and PFOA in the Tennessee River. *Environ. Sci. Technol.* 36, 1681-1685.
Hatfield, T. (2001). Screening studies on the aqueousphotolytic degradation of perfluorooctanoic acid (PFOA). 3M Environmental Laboratory. Lab request number E-00-2192. St. Paul, Minn.
Key, B. D., Howell, R. D., and Criddle, C. S. (1997). Fluorinated Organics in the Biosphere. *Environ. Sci. Technol.* 31, 2445-2454.
Kannan, K., Newsted, J., Halbrook, R. S., and Giesy, J. P. (2002). Perfluorooctanesulfonate and related fluorinated hydrocarbons in mink and river otters from the United States. *Environ. Sci. Technol.* 36, 2566-2571.
Maisey et al. Atlas of Clinical Positron Emission Tomography; London, 1999.
Mawn M. P. et al. Determination of extractable perfluorooctanoic acid (PFOA) in water, sweat stimulant, saliva stimulant, and methanol from textile carpet samples by LC/MS/MS; *Analyst* 130, 670-678 (2005).
Olsen, G. W., Hansen, K. J., Stevenson, L. A., Burris, J. M., and Mandel, J. H. (2003). Human donor liver and serum concentrations of perfluorooctanesulfonate and other perfluorochemicals. *Environ. Sci. Technol.* 37, 888-891.
Reich I. L. et al. Synthesis of $^{14}$C-labeled perfluorooctanoic and perfluorodecanoic acids; purification of perfluorodecanoic acid; *J. Labelled Apd. Radiopharm.* 24, 1235-1244 (1987).
Seeram et al. Computed Tomography: Physical Principles, Clinical Applications, and Quality Control; W B Saunders, 2001.
Vanden Heuvel J. P. et al. Tissue distribution, metabolism, and elimination of perfluorooctanoic acid in male and female rats; *J. Biochem. Toxicol.* 1991, 6(2): 83-92.
Vanden Heuvel J. P. et al. Renal excretion of perfluorooctanoic acid in male rats; inhibitory effect of testosterone; *J. Biochem. Toxicol.* 7, 31-36 (1992).
Vanden Heuvel J. P. et al. Covalent binding of perfluorinated fatty acids to proteins in the plasma, liver and testes of rats; *Chemico-Biol. Interact.* 82, 317-328 (1992).
Von Schulthess et al. Clinical Molecular Anatomic Imaging; Lippincott Williams & Wilkins, 2003.
Wang N. et al. Aerobic biotransformation of 14C-labeled 8-2 telomer B alcohol by activated sludge from a domestic sewage treatment plant; *Environ. Sci. Tech.* 39, 531-538 (2005).

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A polyfluorinated compound useful as an imaging tracer suitable for administration to a subject or a sample, the compound of the formula:

$$CF_3(CF_2)_n R^1 \qquad (I)$$

where:
R$^1$ is —C(O)OR$^2$, -QR$^3$, X, C$_1$-C$_{30}$ alkyl, C$_1$-C$_{30}$ haloalkyl, C$_1$-C$_{30}$ alkoxyl, or C$_1$-C$_{30}$ perhaloalkyl;

$R^2$ is $M^{Z+}$, H, $C_1$-$C_{12}$ alkyl, $C_1$-$C_{12}$ alkyl, $C_1$-$C_{12}$ perhalo alkyl, $C_6$-$C_{30}$ aryl, $C_6$-$C_{30}$ perhaloaryl, and a substituted form thereof where one or more protons or halogens is replaced with a plasma solubility enhancing moiety of or -$QR^3$;

$R^3$ is H or F;

Q is O or S;

$M^{Z+}$ is a cation that forms a net neutral compound with an anionic $(CF_3(CF_2)_nC(O)O^-)_Z$ and is an alkali metal cation, an alkali earth cation, a transition metal cation, ammonium, and aluminum cations;

Z is an integer value of between 1 and 3 inclusive;

X is a fluorine, chlorine, bromine or iodine atom;

halo denotes a replacement of at least one and not all protons with X;

perhalo denotes a replacement of all protons with X; and n is an integer value of between 1 and 30 inclusive, wherein the Formula (I) comprises at least two $^{18}F$ atoms.

2. A polyfluorinated compound useful as an imaging tracer suitable for administration to a subject or a sample, the compound of the formula:

  (I)

where:

$R^1$ is —$C(O)OR^2$; n is 5-7 inclusive; and $R^2$ is H;

wherein the Formula (I) comprises at least one $^{18}F$ atom.

3. The compound of claim 2 wherein the Formula (I) consists of a single $^{18}F$ atom.

4. A polyfluorinated compound useful as an imaging tracer suitable for administration to a subject or a sample, the compound of the formula:

  (I)

where:

$R^1$ is —$C(O)OR^2$; n is 5-7 inclusive; $R^2$ is $M^{1+}$, $M^{1+}$ is an alkali metal cation or ammonium;

wherein the Formula (I) comprises at least one $^{18}F$ atom.

5. A polyfluorinated compound useful as an imaging tracer suitable for administration to a subject or a sample, the compound of the formula:

  (I)

where:

$R^1$ is —$C(O)OR^2$, n is 5-7 inclusive, $R^2$ is $C_1$-$C_4$ alkyl, $C_1$-$C_4$ perfluoroalkyl, $C_6$ aryl, $C_6$ perfluoroalkyl, or the substituted form thereof;

wherein the Formula (I) comprises at least one $^{18}F$ atom.

6. The compound of claim 5 wherein $R^2$ is the substituted form of $C_1$-$C_6$ perfluoroalkyl.

7. The compound of claim 6 wherein the plasma enhancing moiety is -$QR^3$ and Q is O.

8. The compound of claim 7 wherein $R^3$ is H.

9. The compound of claim 7 wherein $R^3$ is F or H.

10. A composition comprising the compound of claim 1 and a pharmaceutically acceptable carrier, wherein the carrier is formulated as an injectable fluid, an aerosol, a cream, a gel, a pill, a capsule, or a syrup.

11. The compound of claim 5 wherein the Formula (I) consists of a single $^{18}F$ atom.

12. A composition comprising the compound of claim 2 further comprising a carrier, wherein the carrier is formulated as an injectable fluid, an aerosol, a cream, a gel, a pill, a capsule, or a syrup.

13. A composition comprising the compound of claim 4 further comprising a carrier, wherein the carrier is formulated as an injectable fluid, an aerosol, a cream, a gel, a pill, a capsule, or a syrup.

14. A composition comprising the compound of claim 5 further comprising a carrier, wherein the carrier is formulated as an injectable fluid, an aerosol, a cream, a gel, a pill, a capsule, or a syrup.

* * * * *